US00PP14373P29

(12) United States Plant Patent
Trees

(10) Patent No.: US PP14,373 P2
(45) Date of Patent: Dec. 16, 2003

(54) JAMESBRITTENIA PLANT NAMED 'BALBRENGO'

(50) Latin Name: *Jamesbrittenia grandiflora*
Varietal Denomination: Balbrengo

(75) Inventor: Scott C. Trees, Shell Beach, CA (US)

(73) Assignee: Ball Floraplant, a division of Ball Horticultural Company, West Chicago, IL (US)

( * ) Notice: Subject to any disclaimer, the term of this patent is extended or adjusted under 35 U.S.C. 154(b) by 0 days.

(21) Appl. No.: 10/329,804

(22) Filed: Dec. 26, 2002

(51) Int. Cl.[7] ..... A01H 5/00
(52) U.S. Cl. ..... Plt./263

(58) Field of Search ..... Plt./263

(56) References Cited

U.S. PATENT DOCUMENTS

PP12,574 P2 * 4/2002 Yates ..... Plt./263
PP12,576 P2 * 4/2002 Yates ..... Plt./263
PP12,617 P2 * 5/2002 Yates ..... Plt./263

* cited by examiner

*Primary Examiner*—Bruce R. Campell
*Assistant Examiner*—W C Haas
(74) *Attorney, Agent, or Firm*—Wood, Phillips, Katz, Clark & Mortimer

(57) ABSTRACT

A new and distinct Jamesbrittenia plant named 'Balbrengo', characterized by its deep lavender colored flowers, spreading, trailing habit, and dark green leaves.

1 Drawing Sheet

Latin name of the genus and species of plant claimed: *Jamesbrittenia grandiflora.*
Variety denomination: 'Balbrengo'.

BACKGROUND OF THE INVENTION

The present invention comprises a new and distinct Jamesbrittenia plant, botanically known as *Jamesbrittenia grandiflora*, and hereinafter referred to by the name 'Balbrengo'.

'Balbrengo' originated from the open pollination of an unnamed *Jamesbrittenia grandiflora* (not patented) during October, 2000. The new cultivar was discovered by the inventor during February 2001, in a controlled environment at Arroyo Grande, Calif.

Asexual reproduction of the new cultivar, in Arroyo Grande, Calif. and West Chicago, Ill., by terminal tip cuttings, has demonstrated that the characteristics of the new cultivar as herein described are firmly fixed and retained through successive generations of such asexual propagation.

SUMMARY OF THE INVENTION

It was found that the cultivar of the present invention:

(a) exhibits deep lavender colored flowers, (b) forms dark green foliage, and (c) exhibits a spreading and trailing growth habit.

The new cultivar of the present invention can be compared to Penny Candy™ 'Violet' (not patented). In side-by-side comparisons, plants of the new cultivar exhibit a shorter growth habit, fewer branches, longer internodes and slightly larger leaves than Penny Candy™ 'Violet'.

BRIEF DESCRIPTION OF PHOTOGRAPH

The accompanying photographs show as nearly true as it is reasonably possible to make the same in color illustrations of this type, typical flower and foliage characteristics of the new cultivar. Colors are as accurately represented as can be made by conventional photography. The plants were grown in 10 cm pots for 10 weeks in a greenhouse at West Chicago, Ill., U.S.A.

DETAILED BOTANICAL DESCRIPTION

Figure 1:
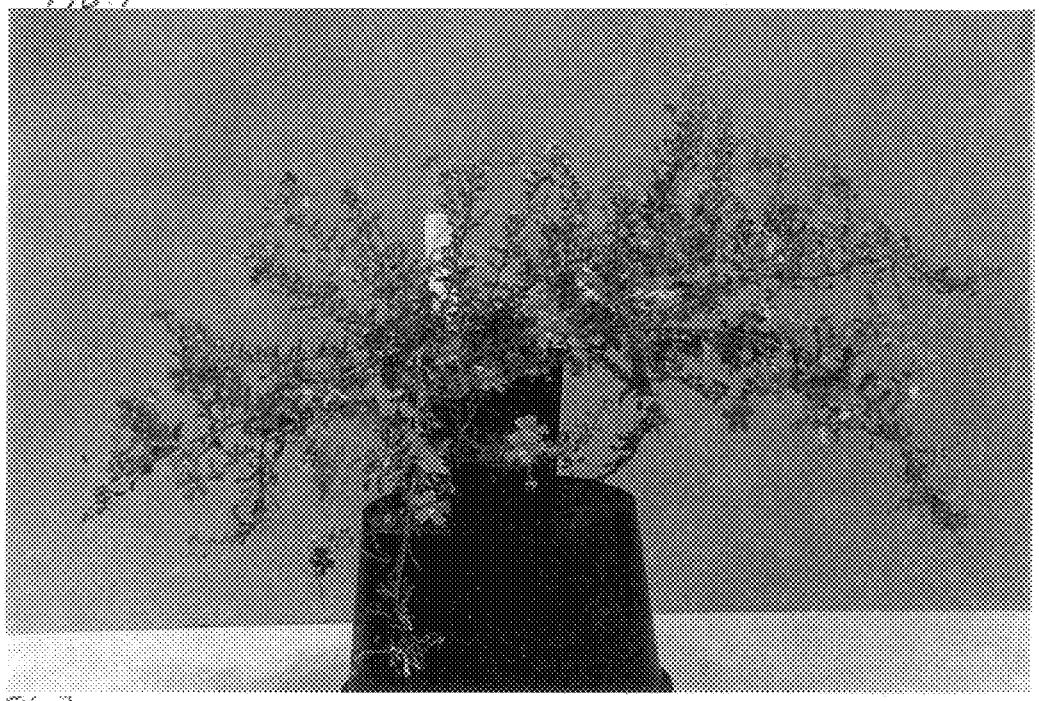
FIG. 1 illustrates the overall plant form of 'Balbrengo'.
Figure 2:
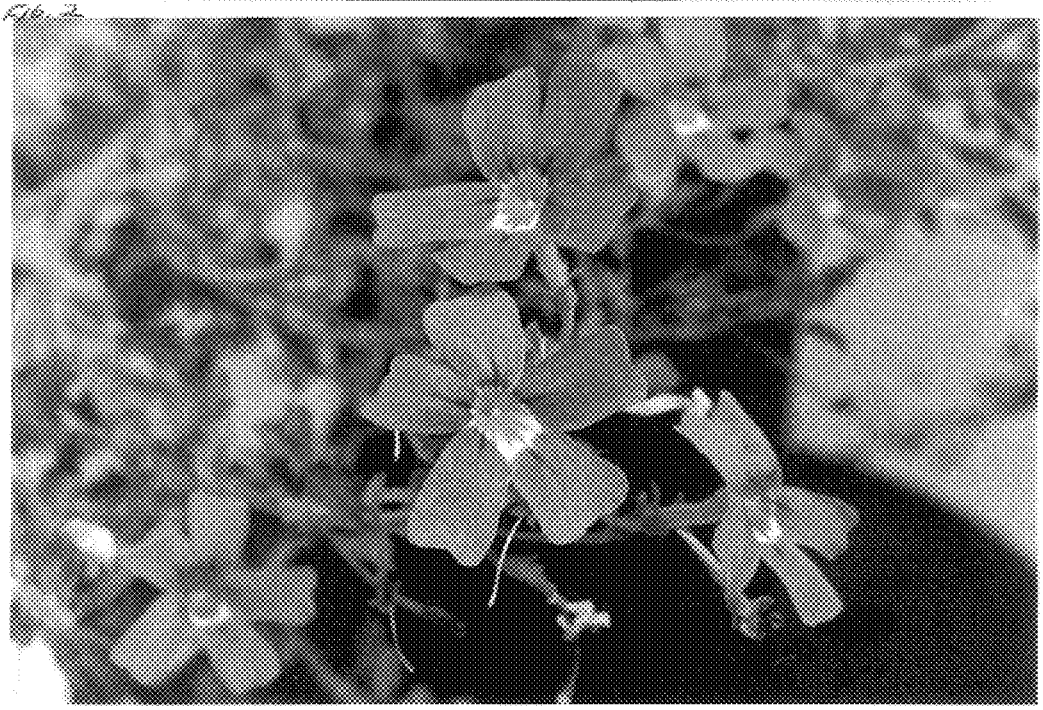
FIG. 2 illustrates close-up view of individual flowers of 'Balbrengo'.

The cultivar 'Balbrengo' has not been observed under all possible environmental conditions to date. Accordingly, it is possible that the phenotype may vary somewhat with variations in the environment, such as temperature, light intensity, and day length. The chart used in the identification of colors described herein is The R.H.S. Colour Chart of The Royal Horticultural Society, London, England. The color values were determined on Oct. 15, 2002. The readings were taken between 1:00 and 3:00 p.m. under natural daylight conditions. The plants were produced from cuttings taken from stock plants and were grown in a double poly carbonate covered greenhouse under conditions comparable to those used in commercial practice while utilizing a soilless growth medium and maintaining temperatures of approximately 65–75° F. during the day and approximately 55–60° F. during the night and light levels of approximately 4,000 to 8,000 footcandles. Plants used for the following descriptions and measurements were grown for 10 weeks from rooted cuttings.

Classification:
*Botanical.*—*Jamesbrittenia grandiflora* cultivar 'Balbrengo'.
*Common name.*—Bacopa.

Parentage: Open pollination of unnamed *Jamesbrittenia grandiflora* (not patented).

Propagation:
*Type cutting.*—Terminal tip.
*Time to initiate roots.*—Approximately 7 to 10 days.

*Time to develop roots.*—Approximately 21 to 30 days.

*Root description.*—Fibrous, branching.

Plant description:

*Habit of growth.*—Moderately vigorous with good basal branching. Pinching improves basal branching. A mature plant, 10 weeks after the planting of a rooted cutting, commonly measures approximately 17.2 cm in height and approximately 63.3 cm in diameter with an average of 6.8 branches.

*Form.*—Spreading and trailing.

*Stem.*—Length: Approximately 42.1 cm. Diameter: Approximately 2 mm. Texture: Pubescent with short hairs. Color: 144A. Internode length at middle of branch is approximately 2.4 cm.

*Foliage.*—Fragrance: Slightly pungent. Form: Simple. Arrangement: Opposite, at an acute angle to the stem. Shape: Ovate with lobed to dentate margin, acute apex and attenuate base. Upper and lower surfaces are sparsely pubescent with lower veins moderately pubescent. Leaf length is approximately 1.5 cm and width is approximately 1.4 cm. Upper surfaces of both young and mature foliage is 146A, lower surfaces of both young and mature foliage is 146B. Both upper and lower surfaces have pinnate venation closest to 144C. Petiole length is approximately 6 mm, diameter is approximately 1 mm, surface is densely pubescent and color is closest to N144C.

Flowering description:

*Type.*—Annual.

*Flowering habit.*—Freely flowering.

*Natural flowering season.*—Year round in greenhouse environment; April through October in outdoor garden.

*Flower type.*—Solitary, axillary, salverform. Flowers are persistent.

*Peduncle.*—Strong, densely pubescent, at an acute angle to the stem, Length: Approximately 2 cm. Diameter: Less than 1 mm. Color: 144A.

*Bud.*—Club shaped, approximately 1.1 cm in length, 7 mm in diameter. Color: N88C.

*Flower description.*—Non-fragrant. Corolla is round, approximately 3 mm in diameter composed of five (5) flat,rectangular shaped petals. Petals are approximately 9 mm long and 5 mm wide, have an entire margin and flat to somewhat emarginate tip. Color of upper surface of lobes when flower is opening and when fully opened is N81B with base of 144D and venation of N81A at base. Color of lower surface of lobes both when opening and when fully opened is N81D. Corolla tube is approximately 1.2 cm in length, 3 mm in diameter and pubescent on both inner and outer surface. Color of inner surface: 25A. Color of outer surface: 13C.

*Calyx.*—Five parted tube fused at base. Approximately 4 mm in length. Sepals are linear, less than 1 mm in width, have an acute apex, entire margin. The both surfaces are densely pubescent and 143C.

*Reproductive organs.*—Androecium: There are 4 stamens fused to the inside of the corolla tube. Anther-length: Approximately 1 mm. Anther color: 11A. Pollen amount: Abundant. Pollen color: 12A. Gynoecium: One pistil, 1.1 cm in length. Stigma length: Approximately 2 mm. Stigma color: N144A. Style length: Approximately 7 mm. Style color: N144B. Ovary diameter: Approximately 1 mm. Ovary color: N144C. Seed production: Seed production has not been observed. Disease resistance: Resistance to pathogens has not been observed.

I claim:

1. A new and distinct *Jamesbrittenia grandiflora* plant named 'Balbrengo' substantially as herein shown and described, which:

(a) exhibits deep lavender colored flowers, (b) forms dark green foliage, and (c) exhibits a spreading and trailing growth habit.

* * * * *